(12) United States Patent
Chadeayne (10) Patent No.: US 12,180,157 B2
(45) Date of Patent: Dec. 31, 2024

(54) CRYSTALLINE BUFOTENIDINE COMPOUNDS

(71) Applicant: CAAMTECH, INC., Issaquah, WA (US)

(72) Inventor: Andrew R Chadeayne, Issaquah, WA (US)

(73) Assignee: CAAMTECH, INC, Issaquah, WA (US)

( * ) Notice: Subject to any disclaimer, the term of this patent is extended or adjusted under 35 U.S.C. 154(b) by 0 days.

(21) Appl. No.: 18/261,395

(22) PCT Filed: Jan. 13, 2022

(86) PCT No.: PCT/US2022/012237
§ 371 (c)(1),
(2) Date: Jul. 13, 2023

(87) PCT Pub. No.: WO2022/155284
PCT Pub. Date: Jul. 21, 2022

(65) Prior Publication Data
US 2024/0043380 A1    Feb. 8, 2024

Related U.S. Application Data

(60) Provisional application No. 63/137,378, filed on Jan. 14, 2021.

(51) Int. Cl.
| *C07D 209/14* | (2006.01) |
| *A61K 45/06* | (2006.01) |
| *C12P 17/10* | (2006.01) |

(52) U.S. Cl.
CPC ............ *C07D 209/14* (2013.01); *A61K 45/06* (2013.01); *C12P 17/10* (2013.01)

(58) Field of Classification Search
CPC .... C07D 209/14; A61K 45/06; A61K 31/585; A61K 31/4045; C12P 17/10; A61P 35/00; A61P 3/10; A61P 15/00; A61P 15/02; A61P 25/00; A61P 25/04; A61P 29/00; C07B 2200/13
See application file for complete search history.

(56) References Cited

U.S. PATENT DOCUMENTS

| 2002/0173511 A1* | 11/2002 | Wurtman ............. A61K 31/155 |
| | | 514/657 |
| 2018/0221396 A1 | 8/2018 | Chadeayne |
| 2019/0142851 A1 | 5/2019 | Chadeayne |

FOREIGN PATENT DOCUMENTS

| CN | 110776454 A | 2/2020 |
| WO | 02/38142 A2 | 5/2002 |

OTHER PUBLICATIONS

Morissette, High-throughput crystallization: polymorphs, salts, co-crystals, and solvates of pharmaceutical solids, Advanced Drug Delivery Reviews, 2004, 56, pp. 275-300 (Year: 2004).*

(Continued)

*Primary Examiner* — Savitha M Rao
*Assistant Examiner* — Andrew P Lee
(74) *Attorney, Agent, or Firm* — RAPHAEL BELLUM PLLC (57) ABSTRACT

The disclosure relates to crystalline form 1 of 5-hydroxy-N,N,N-trimethyl-tryptammonium (5-HTQ) iodide, and to pharmaceutical compositions containing the compound and to methods of treatment using it.

4 Claims, 3 Drawing Sheets

(56) References Cited

OTHER PUBLICATIONS

Dolomanov et al., (2009) "OLEX2: A complete structure solution, refinement and analysis program," J. Appl. Cryst. 42, 339-341.
Sheldrick, (2015) "Crystal structure refinement with SHELXL," Acta Cryst., C71, 3-8.
Sheldrick, (2015) "SHELXT—Integrated space-group and crystal structure determination," Acta Cryst., A71, 3-8.
Bauer, "Hamilton Morris on 5-MeO-DMT, the Entourage Effect, and Protecting Toads", Apr. 15, 2020.
Davis et al., "5-methoxy-N,N-dimethyltryptamine (5-MeO-DMT) used in a naturalistic group setting is associated with unintended improvements in depression and anxiety," Am. J. Drug Alcohol Abuse., 45(2), 161-169.
Etter et al., (1990). "Graph-set analysis of hydrogen-bond patterns in organic crystals," Acta Cryst., B46, 256-262.
Uthaug et al., (2019) "A single inhalation of vapor from dried toad secretion containing 5-methoxy-N,N dimethyltryptamine (5-MeO-DMT) in a naturalistic setting is related to sustained enhancement of satisfaction with life, mindfulness-related capacities, and a decrement of psychopathological symptoms," Psychopharmacology, 236, 2653-2666.
Westrip, (2010) "publCIF: software for editing, validating and formatting crystallographic information files," J. Appl. Cryst. 43, 920-925.
Adhikari et al., (2015) "Calixarene-Mediated Liquid Membrane Transport of Choline Conjugates 2: Transport of Drug-Choline Conjugates and Neurotransmitters," Eur. J. Org. Chem., 2015(12), 2683-2690.
International Preliminary Report on Patentability in International Application No. PCT/US2022/012237 dated Jul. 4, 2023.
Weiland et al., (1934) "The constitution of bufotenine and bufotenidine. About toad toxins. VII," European Journal of Organic Chemistry, 513, 1-25.
Daly et al., (1966) "The Chemorelease of Norepinephrine from Mouse Hearts. Structure-Activity Relationships. I. Sympathomimetic and Related Amines," J. Med. Chem., 9, 3, 273-280.
Barlow, R. B. et al., "Actions of Some Analogues of 5-Hydroxytryptamine on the Isolated Rat Uterus and the Rat Fundus Strip Preparations," British Journal of Pharmacology, 1959, vol. 14, pp. 265-272.

International Search Report and Written Opinion in International Application No. PCT/US2022/012237 filed Jan. 13, 2022.
Chadeayne et al., "Norpsilocin: freebase and fumarate salt", Acta Cryst. (2020). E76, 589-593.
Bauer, "Two New Crystalline Forms of Norpsilocin", Apr. 23, 2020.
Database Registry, "1H-Indole-3-ethanaminium, 5-hydroxy-N,N,N-trimethyl-, iodide", Chemical Abstracts Service, Database Accession No. 5787-02-0, Nov. 16, 1984.
Bernstein (2002), "Chapter 1.2.3: Conventions for naming polymorphs", Polymorphism in Molecular Crystals, 8.
Wieland et al. (1931), "über basische Inhaltsstoffe des Hautsekrets der Kröte" Berichte Der Deutschen Chemischen Gesellschaft Abteilung B:Abhandlungen, 64(8), 2099-2103 (the alleged relevance of this document is discussed on pp. 4-6 of the Extended European Search Report in European Application No. EP22740031.4 dated Apr. 12, 2024, which is submitted herewith).
Stoll et al. (1955), "Eine neue Synthese von Bufotenin und verwandten Oxy-tryptaminen", Helvetica Chimica Acta, 38(6), 1452-1472 (the alleged relevance of this document is discussed on pp. 4-6 of the Extended European Search Report in European Application No. EP22740031.4 dated Apr. 12, 2024, which is submitted herewith).
Collins III et al. (2017), "Supplementary Information: Calixarene-mediated liquid membrane transport of choline conjugates 3: the effect of handle variation on neurotransmitter transport", Bioorg. Med. Chem. Lett. 27(13), 2953-2956, 1-17.
Watkins et al. (1997), "Reversal of spinal cord non-opiate analgesia by conditioned anti-analgesia in the rat", Pain, 71(3), 237-247.
Extended European Search Report in European Application No. EP22740031.4 dated Apr. 12, 2024.
Liu et al., "Role of 5-HT receptors in neuropathic pain: therapeutic implications," Pharmacological Research, 2020, 159, 104949.
Chadeayne et al., "Bis(4-acetoxy-N,N-dimethyltryptammonium) fumarate: a new crystalline form of psilacetin, an alternative to psilocybin as a psilocin prodrug," Acta Cryst., 2019, E75, 900-902.
Carhart-Harris et al., "The Therapeutic Potential of Psychedelic Drugs: Past, Present, and Future," Neuropsychopharmacol., 2017, 42, 2105-2113.
Byrn et al., "Pharmaceutical Solids: A Strategic Approach to Regulatory Considerations" Pharma. Res., 1995, 12, 7, 945-954.
Ciara, "Crystalline Polymorphism of Organic Compounds" Topics in Current Chemistry, 1998, 198, 163-208.
Bavin, "Polymorphism in Process Development" Chemistry and Industry, 1989, 527-529.

\* cited by examiner

CRYSTALLINE BUFOTENIDINE COMPOUNDS

CROSS-REFERENCE TO RELATED APPLICATIONS

This application claims priority to U.S. Provisional Application No. 63/137,378, filed on Jan. 14, 2021, the disclosure of which is incorporated by reference.

TECHNICAL FIELD

This disclosure relates to crystalline form 1 of 5-hydroxy-N,N,N-trimethyl-tryptammonium (5-HTQ) iodide. This disclosure also relates to pharmaceutical compositions containing the compound and methods of treatment using it.

BACKGROUND

Bufotenidine, the N,N,N-trimethyl analog of serotonin was first identified in the toad secretions in 1934 (Wieland et al., 1934). This is one of many indoalkylamines found in the secretions of the Colorado River toad, including bufotenine (5-hydroxy-N,N-di-methyl-tryptamine), 5-MeO-DMT (5-methoxy-N,N-di-methyltryptamine), 5-methoxy-tryptophol, and bufoviridine. Bufotenidine is a potent serotonin 5-$HT_3$ agonist and is a well-known paralytic. One of the strongest psychedelic compounds in these secretions are the O-methylated version of bufotenine [5-methoxy-N,N-dimethyltryptamine (5-MeO-DMT)]. The primary psychedelic in these secretions, 5-MeO-DMT, has been studied individually to treat anxiety and depression (Davis et al., 2019). The inhalation of vaporized dried toad secretions has also been examined in the treatment of depression, anxiety, and stress (Uthaug et al., 2019). As this area of research continues, it will be important to understand the difference between pure 5-MeO-DMT and natural toad secretions, to understand the significance of each component, and examine if an entourage effect is present (Bauer, 2020).

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to crystalline form 1 of 5-hydroxy-N,N,N-trimethyl-tryptammonium (5-HTQ) iodide. Crystalline form 1 of 5-HTQ iodide may be characterized by at least one of: an orthorhombic, $P2_12_12_1$ crystal system space group at a temperature of about 297 K, unit cell dimensions a=8.9944 (4) Å, b=11.3250 (6) Å, and c=14.4042 (7) Å, or an XRPD having peaks at 14.0, 16.8, and 17.6°2θ±0.2°2θ.

The disclosure also relates to compositions comprising crystalline form 1 of 5-hydroxy-N,N,N-trimethyl-tryptammonium (5-HTQ) iodide. The disclosure further relates to pharmaceutical compositions containing a therapeutically effective amount of crystalline form 1 of 5-HTQ iodide and an excipient. In one embodiment the excipient is a pharmaceutically acceptable excipient. The disclosure also relates to pharmaceutical compositions comprising a therapeutically effective amount of crystalline form 1 of 5-HTQ iodide and an excipient, wherein the excipient is a pharmaceutically acceptable carrier.

The disclosure also relates to compositions comprising a combination of, as a first component, crystalline form 1 of 5-HTQ iodide and a second component selected from (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and a pharmaceutically acceptable excipient.

The disclosure further relates to a method of preventing or treating a psychological disorder comprising the step of administering to a subject in need thereof a therapeutically effective amount of crystalline form 1 of 5-HTQ iodide, or of a pharmaceutical composition containing crystalline form 1 of 5-HTQ iodide.

The disclosure further relates to methods of preventing or treating a physical and/or psychological disorder comprising the step of administering to a subject in need thereof an effective amount of crystalline form 1 of 5-HTQ iodide and to administering to a subject in need thereof a pharmaceutical composition containing a therapeutically effective amount of crystalline form 1 of 5-HTQ iodide or a composition according to the disclosure.

The disclosure also relates to methods of preventing or treating inflammation and/or pain comprising the step of administering to a subject in need thereof an effective amount crystalline form 1 of 5-HTQ iodide and to administering to a subject in need thereof a pharmaceutical composition containing a therapeutically effective amount of crystalline form 1 of 5-HTQ iodide or a composition according to the disclosure.

The disclosure also relates to methods of preventing or treating inflammation and/or pain, preventing or treating a neurological disorder, modulating activity of a mitogen activating protein (MAP), modulating neurogenesis, or modulating neurite outgrowth comprising the step of administering to a subject in need thereof a therapeutically effective amount of crystalline form 1 of 5-HTQ iodide, and to administering a pharmaceutical composition or a composition according to the disclosure.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

As used herein, the term "a subject in need thereof" refers to a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

This disclosure relates to crystalline form 1 of 5-hydroxy-N,N,N-trimethyl-tryptammonium (5-HTQ) iodide and to compositions, including pharmaceutical compositions, containing crystalline form 1 of 5-HTQ iodide. The therapeutic uses of crystalline form 1 of 5-HTQ iodide are described below as well as compositions containing them. The preparation of crystalline form 1 of 5-HTQ iodide and the methods used to characterize it are described below. The novel and crystalline form 1 of 5-HTQ iodide compounds of the disclosure may be used to prepare other salts, including pharmaceutically acceptable salts, by anion exchange techniques known in the art to exchange the iodide anion for another desired anion. Crystalline form 1 of 5-HTQ iodide and the methods used to characterize it are described in the examples below.

5-HTQ iodide is a compound of formula (1):

Methods of Treatment and Therapeutic Uses

One embodiment relates to crystalline form 1 of 5-HTQ iodide and the methods and the compositions—particularly the pharmaceutical compositions—using them to regulate the activity of a neurotransmitter receptor by administering a therapeutically effective dose of crystalline form 1 of 5-HTQ iodide. Another embodiment relates to crystalline form 1 of 5-HTQ iodide compounds, according to the disclosure, and the methods and the compositions—particularly the pharmaceutical compositions—of the disclosure are used to treat inflammation and/or pain by administering a therapeutically effective dose of crystalline form 1 of 5-HTQ iodide.

Methods of the disclosure administer a therapeutically effective amount of crystalline form 1 of 5-HTQ iodide to prevent or treat a disease or condition, such as those discussed below for a subject in need of treatment. Crystalline form 1 of 5-HTQ iodide may be administered neat or as a composition comprising crystalline form 1 of 5-HTQ iodide as discussed below.

Crystalline form 1 of 5-HTQ iodide may be used to prevent and/or treat a psychological disorder. The disclosure provides a method for preventing and/or treating a psychological disorder by administering to a subject in need thereof a therapeutically effective amount of crystalline form 1 of 5-HTQ iodide. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Crystalline form 1 of 5-HTQ iodide may be used to prevent and/or treat a brain disorder. The disclosure provides a method for preventing and/or treating a brain disorder by administering to a subject in need thereof a therapeutically effective amount of crystalline form 1 of 5-HTQ iodide. The brain disorder is chosen from Huntington's disease, Alzheimer's disease, dementia, and Parkinson's disease.

Crystalline form 1 of 5-HTQ iodide may also be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline form 1 of 5-HTQ iodide.

Crystalline form 1 of 5-HTQ iodide may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of crystalline form 1 of 5-HTQ iodide. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Crystalline form 1 of 5-HTQ iodide may be used to modulate activity of a mitogen activating protein (MAP), comprising administering a composition of the invention. In one embodiment, the mitogen activating protein (MAP) comprises a MAP kinase (MAPk). MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, Janus Kinase 1 (JAK1), and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-a. In the central nervous system, p38-alpha regulates neuronal death and neurite degeneration, and it is a common target of Alzheimer's disease therapies. JAK1 influences cytokine signaling, including IL-2, IL-4, IFN-alpha/beta, IFN-y, and IL-10, and it is implicated in brain aging. JNK3 is neuronal specific protein isoform of the JNKs. It is involved with the regulation of apoptosis. JNK3 also plays a role in modulating the response of cytokines, growth factors, and oxidative stress.

As used herein, the term "modulating activity of a mitogen activating protein" refers to changing, manipulating, and/or adjusting the activity of a mitogen activating protein. In one embodiment, modulating the activity of a MAP, such as a MAPK, can influence neural health, neurogenesis, neural growth and differentiation, and neurodegenerative diseases.

Crystalline form 1 of 5-HTQ iodide may be used to modulate neurogenesis, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

Crystalline form 1 of 5-HTQ iodide may be used to modulate neurite outgrowth, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

The disclosure also relates to a method of generating a dialkyltryptamine compound in situ in a patient, the method comprising administering crystalline form 1 of 5-HTQ iodide to the patient. The disclosure also relates to methods of generating a dialkyltryptamine compound (e.g., 4-hydroxy-N,N-dimethyltryptamine (psilocin)) comprising providing crystalline form 1 of 5-HTQ iodide, and contacting a 5-hydroxy-N,N,N-trimethyltryptammonium compound (derived from crystalline form 1 of 5-HTQ iodide) with an enzyme in vitro or in vivo, such as an enzyme capable of nitrogen dealkylation (e.g., cytochrome P450 enzymes (CYPs)). The disclosure further relates to methods of generating a dialkyltryptamine compound (e.g., 5-hydroxy-N, N-dimethyltryptamine) in situ in a patient comprising contacting a 5-hydroxy-N,N,N-trimethyltryptammonium compound (derived from crystalline form 1 of 5-HTQ iodide) with an enzyme in the patient capable of nitrogen dealkylation (e.g., cytochrome P450 enzymes (CYPs)).

Compositions

The disclosure also relates to compositions comprising an effective amount of crystalline form 1 of 5-HTQ iodide, and an excipient (e.g., a pharmaceutically-acceptable excipient). In another embodiment, the disclosure also relates to pharmaceutical compositions comprising a therapeutically effective amount of crystalline form 1 of 5-HTQ iodide and a pharmaceutically acceptable carrier (also known as a pharmaceutically acceptable excipient). As discussed above, crystalline form 1 of 5-HTQ iodide may be, for example, therapeutically useful to prevent and/or treat the psychological disorders, brain disorders, pain, and inflammation as well as the other disorders discussed above.

A composition or a pharmaceutical composition of the disclosure may be in any form which contains crystalline form 1 of 5-HTQ iodide. The composition may be, for example, a tablet, capsule, liquid suspension, injectable, topical, or transdermal. The compositions or pharmaceutical compositions generally contain, for example, about 1% to about 99% by weight of crystalline form 1 of 5-HTQ iodide and, for example, 99% to 1% by weight of at least one suitable pharmaceutical excipient. In one embodiment, the composition may be between about 5% and about 75% by weight of crystalline form 1 of 5-HTQ iodide with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, crystalline form 1 of 5-HTQ iodide may be used as the "first purified psilocybin derivative" in the compositions described in US 2018/0221396 A1 and US 2019/0142851 A1. Accordingly, this disclosure provides a composition comprising as a first component: crystalline form 1 of 5-HTQ iodide; and as a second component selected from (a) a serotonergic drug, (b) a purified psilocybin derivative, (c) one or two purified cannabinoids and (d) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

When used in such compositions as a first component comprising crystalline form 1 of 5-HTQ iodide of the disclosure with a second component selected from at least one of (a) a serotonergic drug, (b) a purified psilocybin derivative, (c) a purified cannabinoid, or (d) a purified terpene, the compositions represent particular embodiments of the invention. Compositions having as a first component crystalline form 1 of 5-HTQ iodide of the disclosure with a second component selected from at least one of (e) an adrenergic drug, (f) a dopaminergic drug, (g) a monoamine oxidase inhibitor, (h) a purified erinacine, (i) a purified hericenone represent additional particular embodiments of the invention represented by the compositions having crystalline form 1 of 5-HTQ iodide according to the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments.

A pharmaceutical formulation of the disclosure may comprise, consist essentially of, or consist of (a) crystalline form 1 of 5-HTQ iodide of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, crystalline form 1 of 5-HTQ iodide and the second active compound(s) are each present in a therapeutically effective amount using a purposefully engineered and unnaturally occurring molar ratios. Exemplary molar ratios of crystalline form 1 of 5-HTQ iodide of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing crystalline form 1 of 5-HTQ iodide of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing crystalline form 1 of 5-HTQ iodide of the disclosure may be used in place of a "purified psilocybin derivative" in the compositions described in US 2018/0221396 A1 and US 2019/0142851 A1. Accordingly, the disclosure provides a pharmaceutical formulation comprising as (a) crystalline form 1 of 5-HTQ iodide of the disclosure and at least one second component selected from (a) a purified psilocybin derivative, (b) a purified cannabinoid or (c) a purified terpene; and at least one pharmaceutically-acceptable excipient or at least one other adjuvant, as described herein. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Some exemplary serotonergic drugs include SSRIs and SNRIs. Some examples of specific serotonergic drugs include the following molecules, including any salts, solvates, or polymorphs thereof: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-

Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl]dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (Δ8-THC), Delta-8-tetrahydrocannabinolic acid (Δ8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In one embodiment, a MAOI inhibits the activity of one or both monoamine oxidase A and monoamine oxidase B. In one embodiment a MAOI is a reversible inhibitors of monoamine oxidase A. In one embodiment a MAOI is a drug chosen from isocarboxazid, phenelzine, or tranylcypromine.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of crystalline form 1 of 5-HTQ iodide of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 1. Crystalline form 1 of 5-HTQ iodide of the disclosure may be any one of the exemplary embodiments described above including the crystalline form one of those compounds as disclosed herein.

TABLE 1

| Second Compound | Molar ratio of Crystalline form 1 of 5-HTQ iodide: second compound | Molar ratio of Crystalline form 1 of 5-HTQ iodide: second compound | Molar ratio of a Crystalline form 1 of 5-HTQ iodide: second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |

TABLE 1-continued

| Second Compound | Molar ratio of Crystalline form 1 of 5-HTQ iodide: second compound | Molar ratio of Crystalline form 1 of 5-HTQ iodide: second compound | Molar ratio of a Crystalline form 1 of 5-HTQ iodide: second compound |
|---|---|---|---|
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of crystalline form 1 of 5-HTQ iodide of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of crystalline form 1 of 5-HTQ iodide to the second compound are shown in Table 2. Crystalline form 1 of 5-HTQ iodide of the disclosure may be any one of the exemplary embodiments described above including the crystalline form one of those compounds as disclosed herein.

TABLE 2

| Second Compound | Molar ratio of a Crystalline form 1 of 5-HTQ iodide: second compound | Molar ratio of a Crystalline form 1 of 5-HTQ iodide: second compound | Molar ratio of a Crystalline form 1 of 5-HTQ iodide: second compound |
|---|---|---|---|
| 3,4-methylenedioxymethamphetamine | About 1:100 to about 100:1 | About 1:25 to about 25:1 | About 1:5 to about 5:1 |

TABLE 2-continued

| Second Compound | Molar ratio of a Crystalline form 1 of 5-HTQ iodide: second compound | Molar ratio of a Crystalline form 1 of 5-HTQ iodide: second compound | Molar ratio of a Crystalline form 1 of 5-HTQ iodide: second compound |
|---|---|---|---|
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of crystalline form 1 of 5-HTQ iodide is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L Limbird, eds., McGraw-Hill Press, 155-173 (2001), which is incorporated herein by reference. Crystalline form 1 of 5-HTQ iodide according to the disclosure, compositions and pharmaceutical compositions containing it may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the crystalline form 1 of 5-HTQ iodide or produce undesirable biological effects or otherwise interact in a deleterious manner with any other component(s) of the pharmaceutical composition.

The compositions or pharmaceutical compositions of the disclosure may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, the crystalline form 1 of 5-HTQ iodide according to the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of crystalline form 1 of 5-HTQ iodide of the disclosure in pure form, with a permeation enhancer, with stabilizers (e.g. antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation of crystalline form 1 of 5-HTQ iodide is described below.

Synthesis and Crystallization

5-HTQ iodide was prepared according to literature procedure (Adhikari et al., 2015), and crystals suitable for diffraction study were grown from the evaporation of a methanol solution.

Single crystal data, data collection and structure refinement details are summarized in Table 3.

TABLE 3

| | 5-HTQ iodide |
|---|---|
| Chemical formula | I·$C_{13}H_{19}N_2O$ |
| $M_r$ | 346.20 |
| Crystal system, space group | Orthorhombic, $P2_12_12_1$ |
| Temperature (K) | 297 |
| a, b, c (Å) | 8.9944 (4), 11.3250 (6), 14.4042 (7) |
| V (Å$^3$) | 1467.23 (12) |
| Z | 4 |
| F(000) | 688 |
| $D_x$ (Mg m$^{-3}$) | 1.567 |
| Radiation type | $M_o$ $K_\alpha$ |
| λ (Å) | 0.71073 |
| μ (mm$^{-1}$) | 2.17 |
| Crystal size (mm) | 0.25 × 0.19 × 0.18 |
| Diffractometer | Bruker D8 CMOS |
| Absorption correction | Multi-scan SADABS2016/2 (Bruker, 2016/2) was used for absorption correction. wR2(int) was 0.0650 before and 0.0457 after correction. The Ratio of minimum to maximum transmission is 0.9018. The λ/2 correction factor is not present. |

TABLE 3-continued

| | 5-HTQ iodide |
|---|---|
| $T_{min}$, $T_{max}$ | 0.672, 0.745 |
| No. of measured, independent and observed [I > 2s(I)] reflections | 45268, 2937, 2866 |
| $R_{int}$ | 0.023 |
| $\theta_{max}$, $\theta_{min}$ (°) | 26.4, 2.9 |
| $(\sin \theta/\lambda)_{max}$ (Å$^{-1}$) | 0.625 |
| $R[F^2 > 2\sigma(F^2)]$, $wR(F^2)$, S | 0.013, 0.032, 1.08 |
| w | $1/[\sigma^2(F_o^2) + (0.0105P)^2 + 0.4198P]$ where $P = (F_o^2 + 2F_c^2)/3$ |
| No. of reflections | 2937 |
| No. of parameters | 165 |
| No. of restraints | 2 |
| h, k, l | $-11 \rightarrow 10$, $-14 \rightarrow 14$, $-18 \rightarrow 18$ |
| H-site location | mixed |
| H-atom treatment | H atoms treated by a mixture of independent and constrained refinement |
| $(\Delta/\sigma)_{max}$ | 0.002 |
| $\Delta\rangle_{max}$, $\Delta\rangle_{min}$ (e Å$^{-3}$) | 0.42, −0.37 |
| Absolute Structure | Flack x determined using 1216 quotients [(I+) − (I−)]/[(I+) + (I−)] (Parsons, Flack and Wagner, Acta Cryst. B69 (2013) 249-259). |
| Absolute Structure Parameter | −0.021 (4) |

Data collection: APEX3 (Bruker, 2018); cell refinement: SAINT (Bruker, 2018); data reduction: SAINT (Bruker, 2018); program(s) used to solve structure: SHELXT2014 (Sheldrick, 2015b); program(s) used to refine structure: SHELXL2018 (Sheldrick, 2015a); molecular graphics: OLEX2 (Dolomanov et al., 2009); software used to prepare material for publication: publCIF (Westrip, 2010).

Figure 1:
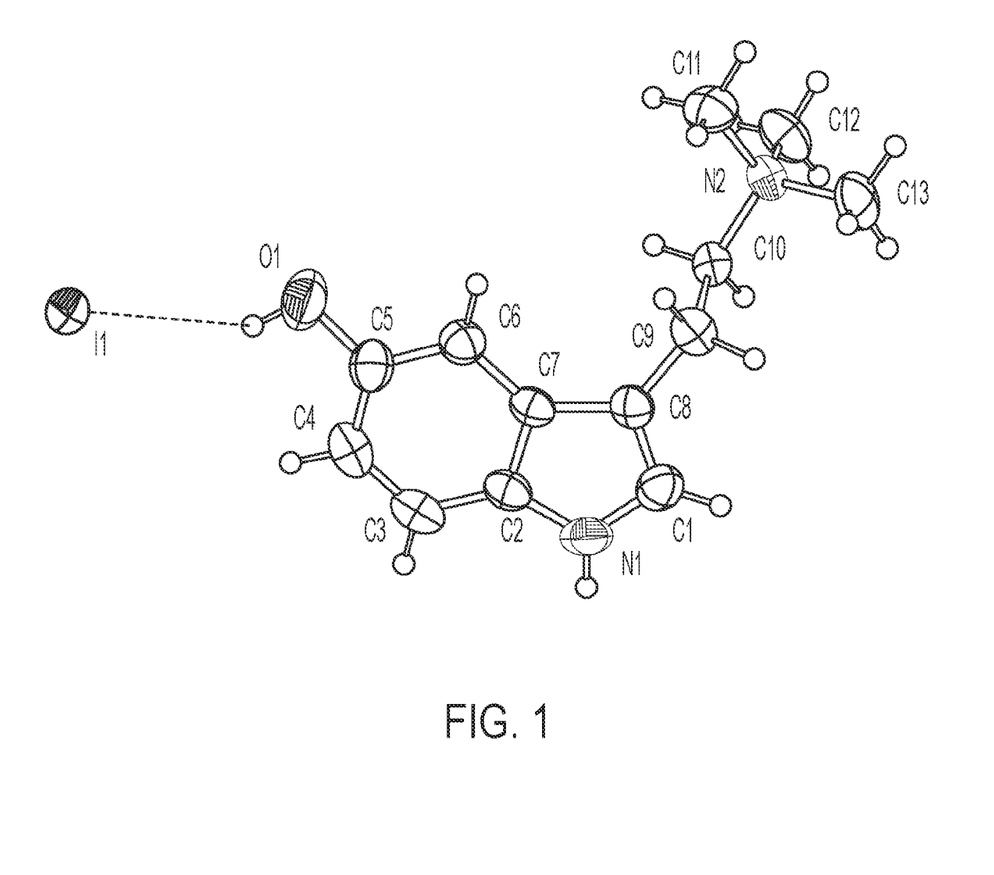
FIG. 1 shows the molecular structure of crystalline form 1 of 5-HTQ iodide, showing the atom labeling.

Crystalline form 1 of 5-HTQ iodine has a single tryptammonium cation and one iodide anion in the asymmetric unit. The molecular structure of crystalline form 1 of 5-HTQ iodide, showing the atom labeling, is shown in FIG. 1. Hydrogen bonds are shown as dashed lines.

In the solid-state structure of bufotenidine iodide, the 5-hydroxy-N,N,N-trimethyl-tryptammonium cation and the iodide anion are held together in the asymmetric unit via O—H . . . I hydrogen bonds (FIG. 1). The cation possesses a near planar indole group with a mean deviation from planarity of 0.010 Å. The ethyl-amino group is turned away from the plane with a C1-C8-C9-C10 torsion angle of 92.6 (3)°. The N—H of the indole ring hydrogen bonds with a symmetry generated iodide. The N—H . . . I and O—H . . . I hydrogen bonds link the ions together in infinite chains along the [100] direction with graph-set notation C12(9) (Etter et al., 1990).

Figure 2:
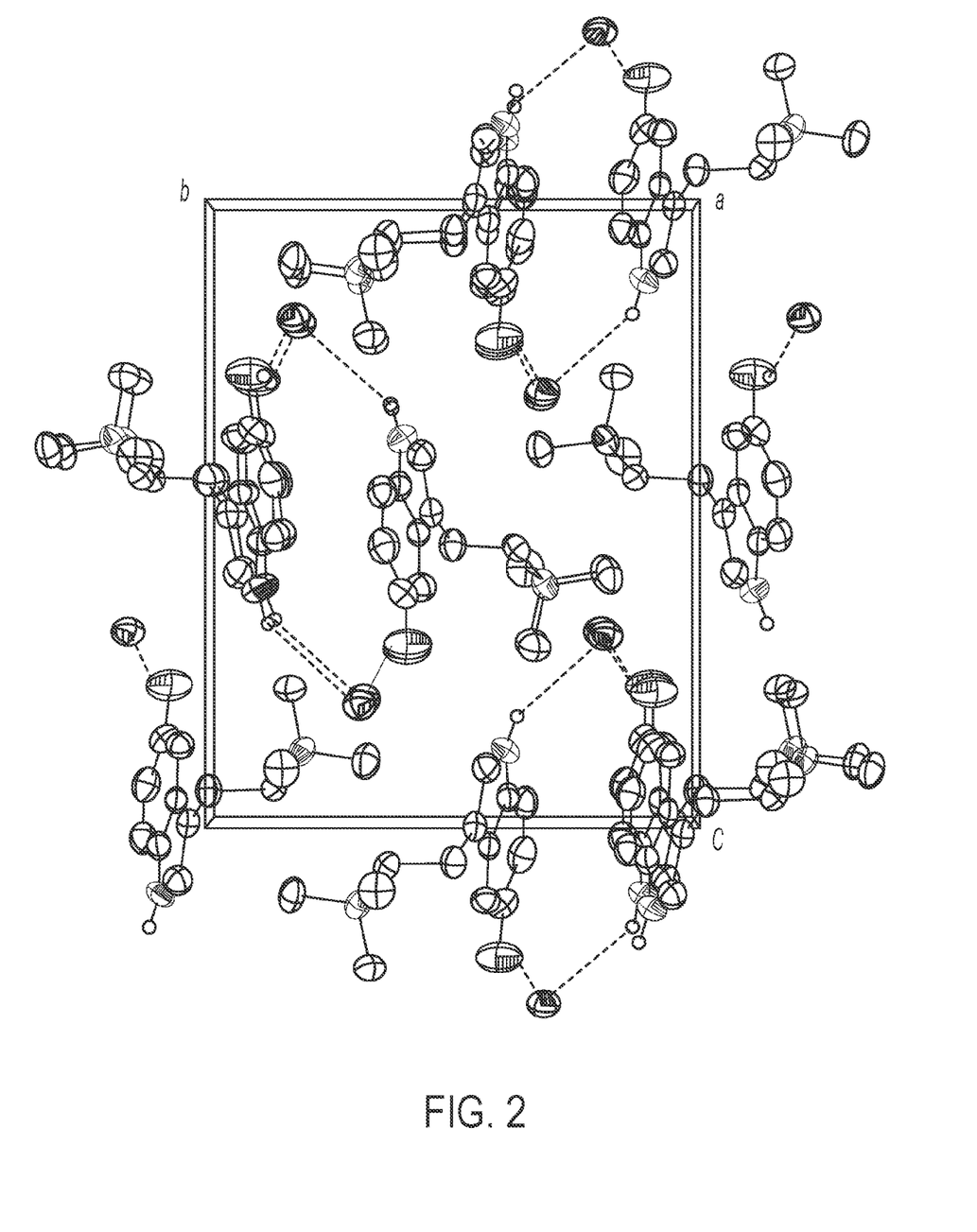
FIG. 2 shows the crystal packing of crystalline form 1 of 5-HTQ iodide.

The crystal packing of crystalline form 1 of 5-HTQ iodide is shown in FIG. 2. Hydrogen bonds are shown as dashed lines.

Figure 3:
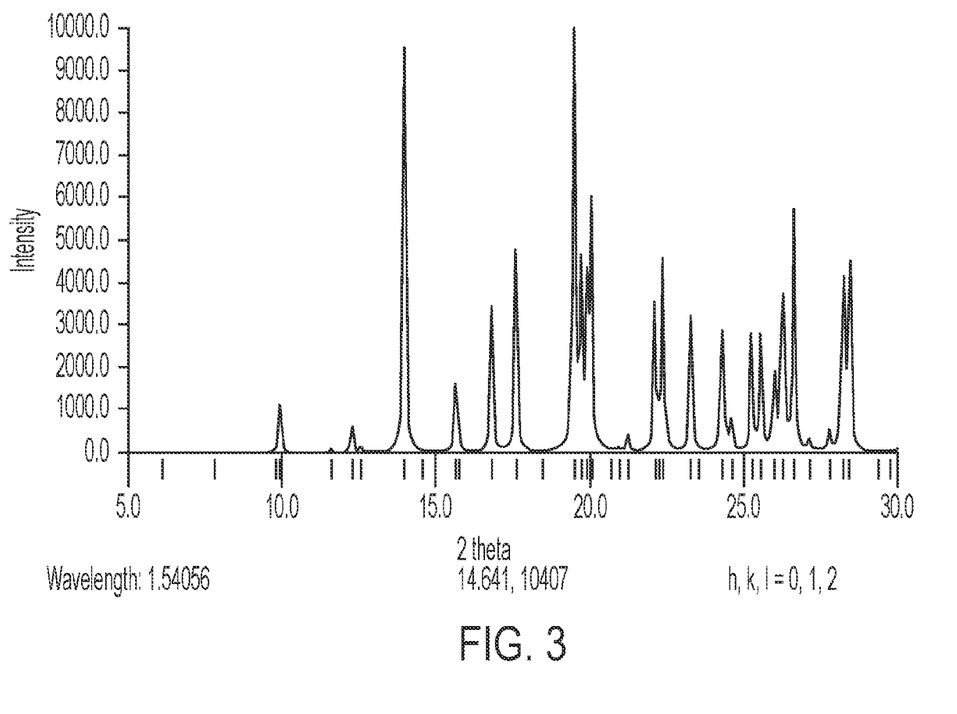
FIG. 3 shows a simulated x-ray powder diffraction (XRPD) of crystalline form 1 of 5-HTQ iodide from its single crystal data.

FIG. 3 is a simulated x-ray powder diffraction (XRPD) of crystalline form 1 of 5-HTQ iodide from its single crystal data. Table 4 lists the angles, °2θ±0.2°2θ, and d-spacing of the peaks identified in the experimental XRPD pattern of FIG. 3. The entire list of peaks, or a subset thereof, may be sufficient to characterize the cocrystal. For example, crystalline form 1 of 5-HTQ iodide may be characterized by at least two peaks selected from the peaks at 14.0, 16.8, and 17.6°2θ±0.2°2θ or their corresponding d-spacing as well as by an XRPD pattern substantially similar to FIG. 3.

TABLE 4

| d-spacing (Å) | 2(Theta deg) | Intensity |
|---|---|---|
| 8.90 | 9.9 | 5405.3 |
| 7.63 | 11.6 | 513.7 |
| 7.20 | 12.2 | 4398.4 |
| 7.04 | 12.6 | 813.2 |
| 6.33 | 14.0 | 92097.6 |
| 6.08 | 14.6 | 158.2 |
| 5.66 | 15.6 | 18294.8 |
| 5.62 | 15.8 | 4048 |
| 5.27 | 16.8 | 48678.8 |
| 5.04 | 17.6 | 72406.4 |
| 4.79 | 18.5 | 308.9 |
| 4.55 | 19.5 | 187507.2 |
| 4.50 | 19.7 | 76731.2 |
| 4.45 | 19.9 | 72692 |
| 4.42 | 20.1 | 114372 |
| 4.29 | 20.7 | 1176.4 |
| 4.24 | 21.0 | 1475.2 |
| 4.18 | 21.2 | 8290.5 |
| 4.01 | 22.1 | 83622.4 |
| 3.99 | 22.3 | 9291.7 |
| 3.97 | 22.4 | 115326.4 |
| 3.81 | 23.3 | 85972.4 |
| 3.66 | 24.3 | 48346.4 |
| 3.65 | 24.4 | 69734.4 |
| 3.62 | 24.6 | 20091.9 |
| 3.60 | 24.7 | 559.9 |
| 3.52 | 25.3 | 88246 |
| 3.48 | 25.6 | 91770 |
| 3.43 | 25.9 | 16803.6 |
| 3.42 | 26.0 | 54766.5 |
| 3.39 | 26.3 | 95404 |
| 3.38 | 26.3 | 76152.8 |
| 3.34 | 26.6 | 26147.5 |
| 3.34 | 26.6 | 178892.4 |
| 3.28 | 27.1 | 9231.0 |
| 3.21 | 27.8 | 16874 |
| 3.16 | 28.2 | 64007.6 |
| 3.15 | 28.3 | 149562.4 |
| 3.13 | 28.5 | 178098.4 |
| 3.04 | 29.4 | 894.7 |

REFERENCES

Adhikari, B. B., Roshandel, S., Fujii, A. & Schramm, M. P. (2015). Eur. J. Org. Chem. 2015, 2683-2690.

Bauer, B. E. (2020). Psychedelic Science Review. https://psychedelicreview.com/hamilton-morris-on-5-meo-dmt-the-entourage-effect-and-protecting-toads/.

Bruker (2018). APEX3, SAINT, and SADABS. Bruker AXS Inc., Madison, Wisconsin, USA.

Davis, A. K., So, S., Lancelotta, R., Barsuglia, J. P. & Griffiths, R. R. (2019). Am. J. Drug Alcohol Abuse, 45, 161-169.

Dolomanov, O. V., Bourhis, L. J., Gildea, R. J., Howard, J. A. K. & Puschmann, H. (2009). J. Appl. Cryst. 42, 339-341.

Etter, M. C., MacDonald, J. C. & Bernstein, J. (1990). Acta Cryst. B46, 256-262.

Sheldrick, G. M. (2015a). Acta Cryst. A71, 3-8.

Sheldrick, G. M. (2015b). Acta Cryst. C71, 3-8.

Uthaug, M. V., Lancelotta, R., van Oorsouw, K., Kuypers, K. P. C., Mason, N., Rak, J., Šuláková, A., Jurok, R., Maryška, M., Kuchař, M., Páleníček, T., Riba, J. & Ramaekers, J. G. (2019). Psychopharmacology, 236, 2653-2666.

Westrip, S. P. (2010). J. Appl. Cryst. 43, 920-925.

Wieland, H., Konz, W. & Mittasch, H. (1934). Justus Liebigs Ann. Chem. 513, 1-25.

The claimed invention is:

1. Crystalline form 1 of 5-hydroxy-N,N,N-trimethyl-tryptammonium (5-HTQ) iodide characterized by at least one of:
   an orthorhombic, $P2_12_12_1$ crystal system space group at a temperature of about 297 K;
   unit cell dimensions a=8.9944 (4) Å, b=11.3250 (6) Å, and c=14.4042 (7) Å;
   an X-ray powder diffraction pattern characterized by at least two peaks selected from 14.0, 16.8, and 17.6°2θ±0.2°2θ; or
   an X-ray powder diffraction pattern substantially similar to FIG. 3.

2. A composition comprising crystalline form 1 of 5-HTQ iodide according to claim 1 and an excipient.

3. A pharmaceutical composition comprising a therapeutically effective amount of crystalline form 1 of 5-HTQ iodide according to claim 1 and a pharmaceutically acceptable excipient.

4. A composition comprising crystalline form 1 of 5-HTQ iodide according to claim 1 and a second component selected from (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, or (i) a purified hericenone.

\* \* \* \* \*